United States Patent [19]
Wilson

[11] Patent Number: 5,787,901
[45] Date of Patent: Aug. 4, 1998

[54] METHOD FOR THE MEASUREMENT OF BLOOD COAGULATION PROPERTIES WITH ABSORBENT MATERIALS

[75] Inventor: Paul E. Wilson, Chapel Hill, N.C.

[73] Assignee: Akzo Nobel N.V., Arnhem, Netherlands

[21] Appl. No.: 789,261

[22] Filed: Jan. 28, 1997

[51] Int. Cl.[6] ............................................. A61B 19/00
[52] U.S. Cl. ................................. 128/898; 600/584
[58] Field of Search ................. 422/56–58; 128/898, 128/760, 765; 604/358, 367; 600/575, 578, 584

[56] References Cited

U.S. PATENT DOCUMENTS

| | | | |
|---|---|---|---|
| 3,658,480 | 4/1972 | Kane et al. | 356/39 X |
| 4,790,979 | 12/1988 | Terminiello et al. | 422/56 |
| 4,818,493 | 4/1989 | Coville et al. | 422/102 |
| 4,980,297 | 12/1990 | Haynes et al. | 128/760 X |
| 5,151,192 | 9/1992 | Matkovich et al. | 604/4 X |
| 5,339,830 | 8/1994 | Blake, III | 128/771 X |
| 5,455,009 | 10/1995 | Volger et al. | 422/102 |
| 5,504,001 | 4/1996 | Gavin et al. | 128/760 X |
| 5,533,518 | 7/1996 | Vogler | 128/760 |
| 5,591,403 | 1/1997 | Gavin et al. | 128/760 X |
| 5,601,995 | 2/1997 | Exner | 422/56 X |

FOREIGN PATENT DOCUMENTS

WO 94/06007 3/1994 WIPO.
WO 96/00395 1/1996 WIPO.

*Primary Examiner*—V. Millin
*Assistant Examiner*—Kelly O'Hara
*Attorney, Agent, or Firm*—Gregory R. Muir

[57] ABSTRACT

A point-of-care device allows for a simple and rapid determination of blood coagulation properties. The device is comprised of an absorbent material and a clotting agent. In operation, a quantity of blood is first allowed to clot, after which remaining serum is allowed to migrate through the absorbent material. The serum migration distance is proportional to the clotting time of the patient sample as routinely determined. The device can be used directly at the bedside of a hospital patient for immediate test results, or can be used for patient self-monitoring.

6 Claims, 12 Drawing Sheets

METHOD FOR THE MEASUREMENT OF BLOOD COAGULATION PROPERTIES WITH ABSORBENT MATERIALS

BACKGROUND OF THE INVENTION

1. Field of the Invention

In view of the severe complications that can result from abnormal blood coagulation, it would be highly desirable to have a rapid test for a patient's blood coagulation potential. Presently, a number of automated machines are available which take a sample of blood, add one or more reagents, and test for the time it takes for the patient blood sample to clot. However, such machines are generally available in, for example, the hospital laboratory, not at a patient's bedside. Therefore, there is a time delay involved in taking the patient's blood sample, labeling the container, arranging for the container to be brought to the laboratory, waiting for the test to be run, arranging to pick up the results of the test, etc. Even if the time delay in getting the results is only a few hours, such a delay may affect the care of a patient with a serious imbalance in the blood clotting mechanism.

For this reason, it would be desirable to have, in addition to sophisticated, automated, laboratory-based devices, a simple coagulation monitor that provides rapid results. Particularly desirable would be a test that could give immediate results at the bedside of the patient and is easy to use so that any hospital staff member could operate the test and get accurate results. An easy to use test that gives fast, accurate results could also serve patients for use at home.

2. Description of the Related Art

The current standard and routine method for determination of blood coagulation potential is embodied in the Prothrombin time (PT) test. For such a test, blood plasma is mixed with a reagent preparation containing an appropriate level of calcium ions and the enzyme tissue factor. The enzyme containing reagent is also termed a thromboplastin. Mechanical or photo-optical means are required to monitor the mixing event and the subsequent formation of a fibrin blood clot. The amount of time (measured in seconds) for clotting to occur is correlated to blood coagulation potential. Abnormal blood plasma samples will require a longer time to clot than normal samples.

The standard methodology has been automated and numerous clotting time devices are commercially available for use in clinical laboratories. In addition to laboratory-based devices, several point-of-care devices are available, some of which are simply miniaturized versions of the laboratory-based devices and some of which employ unique clot detection methodologies. All measure the time needed for a clot to occur.

In WO 9406007, the propensity of a test sample to change from a liquid state to a coagulated state is detected. A sample is applied to an exposed surface of a porous sheet having clotting or lysing agents and which is sandwiched between electrodes which monitor conductivity as the sample spreads. A parameter is measured which is indicative of the extent of spread and/or the rate of spread, which in turn is indicative of the propensity of the sample to coagulate.

In WO 96000395, a device is disclosed wherein an activator region containing a thromboplastin is juxtaposed with a porous element impregnated with fibrinogen, the enzymatic precursor of clottable fibrin. As a thromboplastin-activated sample migrates through the fibrinogen laced region, clot formation occurs and its travel is retarded. This technology is related to the standard method in that a blood sample, having the inherent ability to clot, is induced to clot by an enzyme-containing preparation and the progress to clot formation is monitored by the device.

The present invention is wholly different from clotting time devices that measure the time to clot in that means are provided to allow contact of absorbent material with the plasma sample after clot formation. Clot formation is caused to take place prior to migration of the sample through an absorbent material. In addition, current point-of-care coagulation devices are expensive and technically complicated. Many are too complicated and expensive for home users to purchase. The present invention is uncomplicated and inexpensive.

SUMMARY OF THE INVENTION

In the present invention, it is the properties of the serum component of clotted blood which is measured and related to clotting potential. Such properties may include but are not limited to, serum volume, viscosity, charge, pH and degree of fibrin clot hydration. A goal of the present invention is to examine the properties of a clotted patient sample through measurement of migration distance through absorbent material.

More particularly, in the present invention an absorbent material, such as a filter paper strip, is provided, which has a highly defined serum uptake. A patient's blood sample is treated with clotting agent such as thromboplastin or a mixture of activated silica and phospholipids and is thereby induced to clot. Means are then provided to allow contact of the clotted sample with an absorbent material. Serum, the non-gel portion of the fibrin blood clot, will move through the absorbent material. The migration distance is directly proportional to the prothrombin time as routinely determined.

BRIEF DESCRIPTION OF THE DRAWINGS

A preferred embodiment of the invention will be described in conjunction with the accompanying drawings.

DETAILED DESCRIPTION OF THE INVENTION

Figure 1:
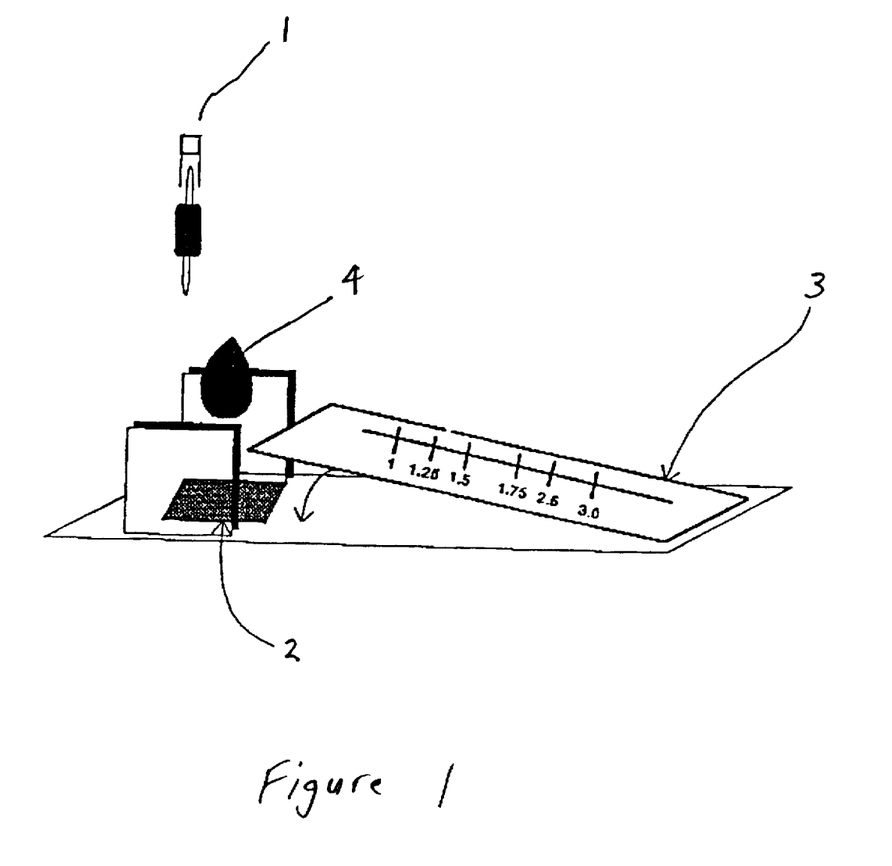
FIG. 1 is an illustration of one embodiment of the present invention utilizing an absorbent material affixed to a scale.

As can be seen in FIG. 1, a capillary dispenser 1 is provided along with a membrane 2, and an absorbent membrane 3 which can be provided with a plastic support. Absorbent membrane 3 can be any suitable absorbent material, such as filter paper (e.g. Schleicher and Schuell #903 paper, a pure cotton linter, white, binderless paper). The preferred serum uptake level for the paper should be in the range of 1–2 microliters per ⅛" disc. Membrane 2 can be provided already impregnated with a clotting agent, or a drop of the clotting agent can be added so as to coat membrane 2. Thereafter, a sample of blood 4 (e.g. from a fingerprick) is drawn into capillary dispenser 1, or other liquid metering device, and added to the thromboplastin, after which a timer can be activated. After a clot has formed (about 2 minutes) an absorbent membrane 3, such as a strip of filter paper, is urged into contact with the clotted drop of blood. The non-clotted portion of the drop of blood, the blood serum, then migrates through the absorbent membrane. Because the volume of serum from the drop of blood is finite, the migration of the serum will end at a particular point along the absorbent membrane, so as to define a "liquid front" on the membrane. The distance of travel of the serum can then be marked and measured, or preferably, the absorbent membrane is ruled so that the position of the liquid front can be easily determined.

Figure 2:
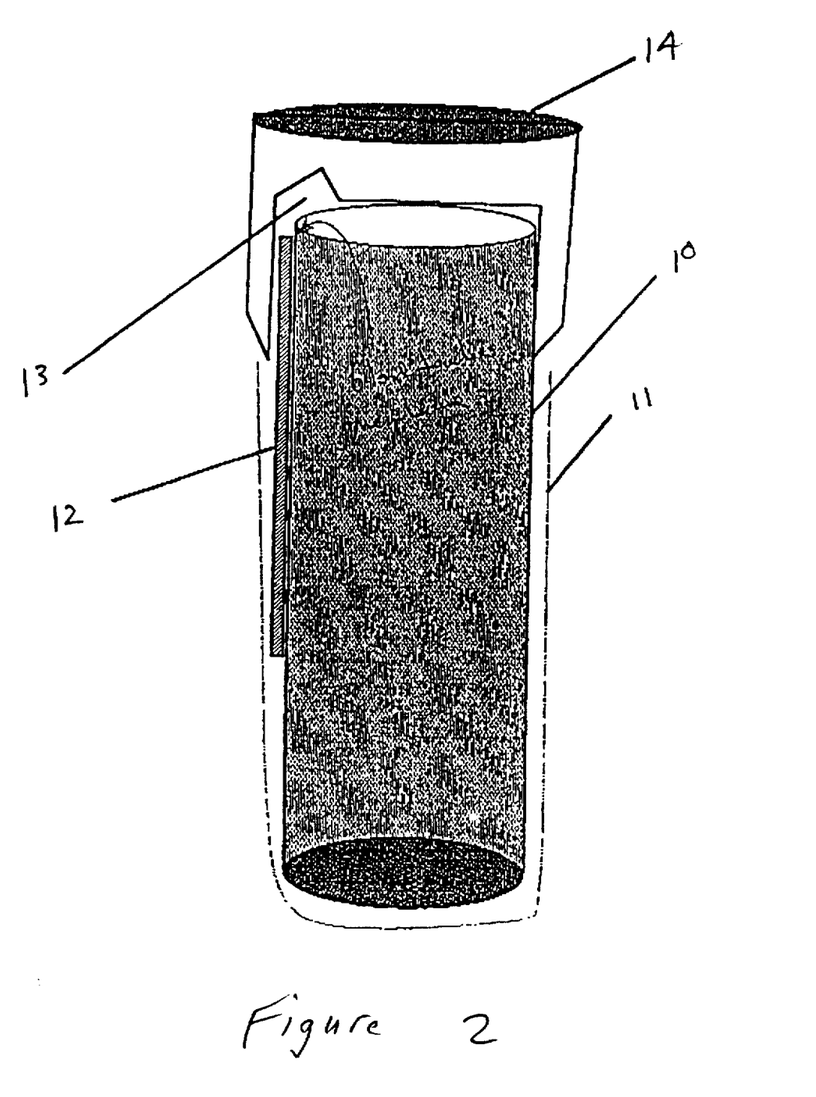
FIG. 2 is an illustration of a second embodiment of the present invention utilizing a blood collection container under vacuum with an absorbent membrane as part of the label.

As can be seen in FIG. 2, a blood vacuum container 10 (e.g. Vacutainer) is illustrated, having a cap 14, a groove 13, an absorbent membrane 12, and an outer covering 11, such as shrink wrap. The user of the device draws blood into the vacuum tube, which tube can contain citrate. The blood and citrate in the tube are then mixed by inversion of the tube. If a coagulation measurement is needed, the user twists the cap, exposing a thromboplastin-treated absorbent membrane, and inverts the tube. A drop of citrated blood accumulates in groove 13 and is absorbed onto the end of the absorbent membrane 12 held in place by cover 11. In this embodiment, the membrane is comprised of two segments. The first segment initiates clotting and the second membrane segment allows for migration of serum. Following clot formation on the thromboplastin-containing membrane, means are provided to allow contact of the second membrane with the clotted sample of blood. Migration of liquid down the membrane 13 is proportional to the prothrombin time and to the International Normalized Ratio (INR) of the sample. After a period of time, the INR of the sample is read from the label of the vacuum container. The cover 11, such as thick shrink wrap, protects the user from exposure to potentially infectious serum which migrates from out of the vacuum container, via groove 13, to the absorbent membrane 12. By the arrangement illustrated in FIG. 2, the user performing the test does not have to open the vacuum tube to perform the test, and the volume of biohazardous waste associated with coagulation testing does not increase as the accouterments of coagulation testing are discarded with the vacuum tube.

In the present invention, the serum which comes into contact with one end of the absorbent material will move through the absorbent material a particular distance. The distance of movement is proportional to the coagulation properties of the plasma sample.

A healthy patient's blood plasma yields serum which migrates a short distance into the absorbent membrane while plasma from a person with abnormal coagulation (such as a coumadinized patient or a factor VII deficient patient) will yield serum which migrates a relatively longer distance into the absorbent strip.

Figure 3:
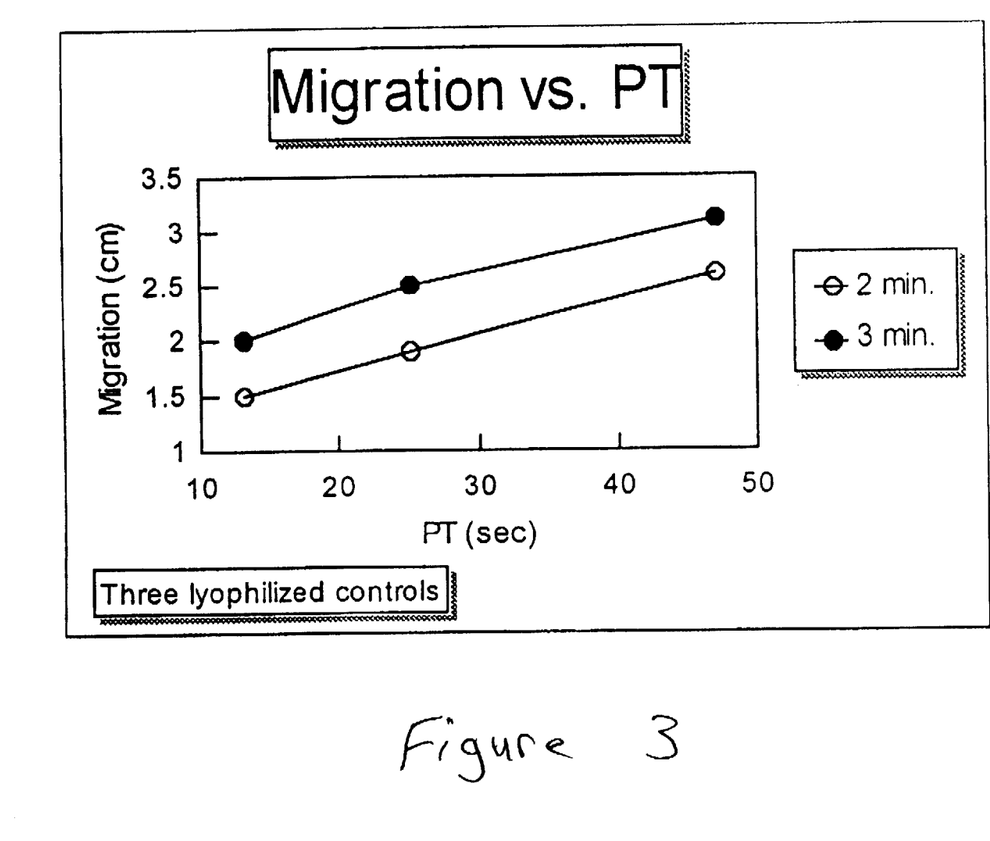
FIG. 3 is a graph of serum migration distance through a cellulose-based absorbent paper strip vs. the prothrombin Time (PT) as routinely determined with data for commercially-available lyophilized control plasmas.

In the present invention, the blood can be clotted using a thromboplastin reagent as for a PT test or with an APTT reagent as for an Activated Partial Thromboplastin Test. It is not beyond the scope of the invention to effect clotting with other agents such as Factor Xa, Russell's viper venom, etc. The following examples help to explain the present invention:

Example 1—Thirty microliters of a commercial thromboplastin preparation (PT-FIB HS, Instrumentation labs) was added to 50 microliters of either Verify 1, Verify 2 or Verify 3 lyophilized control plasma samples (Organon Teknika). The thromboplastin was allowed to react with the plasma samples for 1 minute before an absorbent paper strip was urged into contact with the clotted sample. Cellulosic, white filter paper with a 0.45 micron pore size (MSI) was used. Migration was measured at 2 minutes and at 3 minutes. For comparison, the prothrombin time (PT) was determined on a fibrometer using the same thromboplastin and plasma samples. The results of this test are illustrated in FIG. 3, where it can be seen that there is a linear correlation between the prothrombin time and the distance of migration in the paper.

Figure 4:
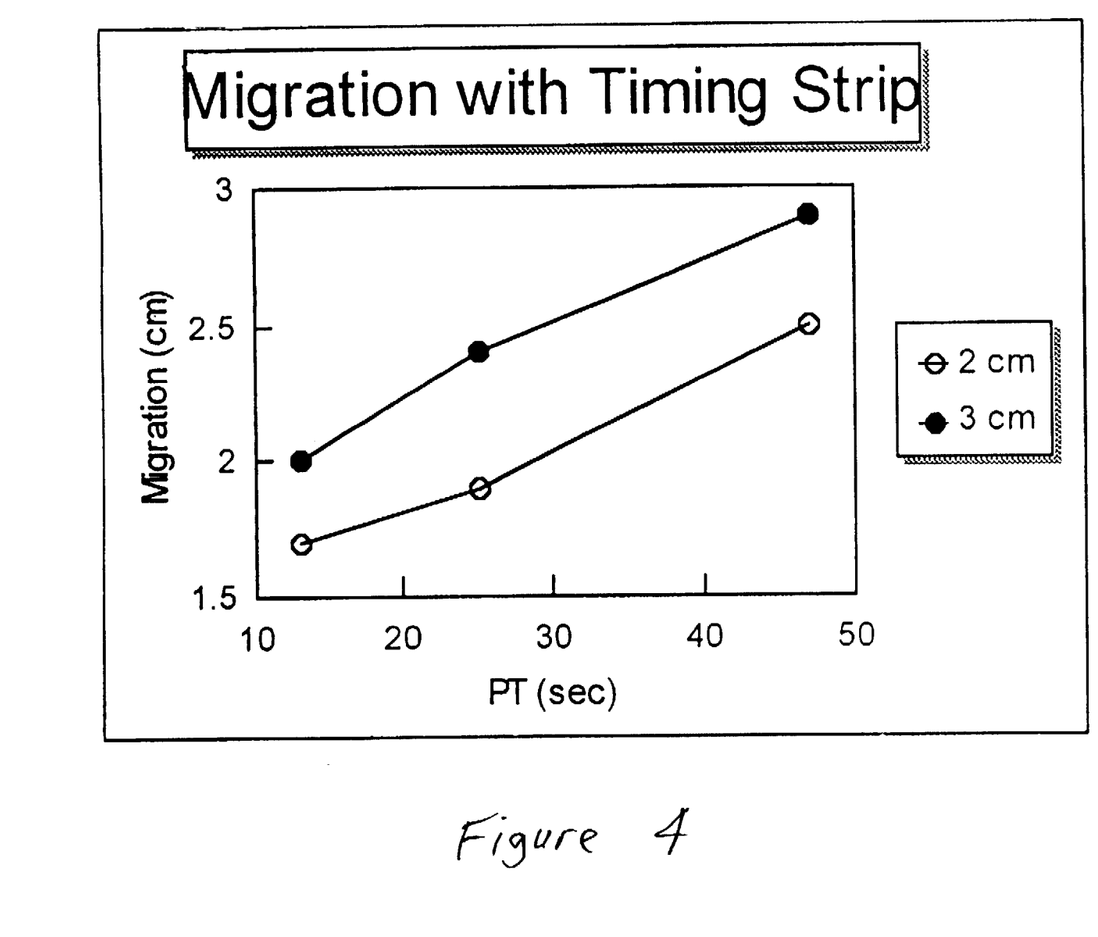
FIG. 4 is a graph of serum migration distance through a cellulose-based absorbent paper strip vs. the prothrombin Time (PT) as routinely determined where the endpoints for this test were determined by simultaneous application of a dye-containing aqueous sample and clotted plasma samples to strips of cellulose-based paper, the dye containing strip functioning as a timing strip, and samples which are commercially available lyophilized control plasmas.

Example 2—In this example, an un-clotted plasma sample was allowed to migrate through a separate absorbent strip (timing strip) to indicate when to mark the endpoint for three other strips. The companion strips measured the coagulation potential of lyophilized controls that were allowed to react with a commercial thromboplastin preparation (Simplastin L, Organon Teknika) for one minute prior to contact with the strips. When the migrating liquid front (water+plasma) on the timing strip reached the 2 and 3 cm mark, the serum fronts on the test strips were read. The prothrombin time for the plasma samples and the thromboplastin were determined using a fibrometer. The results of this test are set forth in FIG. 4, where it can be seen that there is a linear correlation between distance of migration in the paper and the clotting time.

Figure 5:
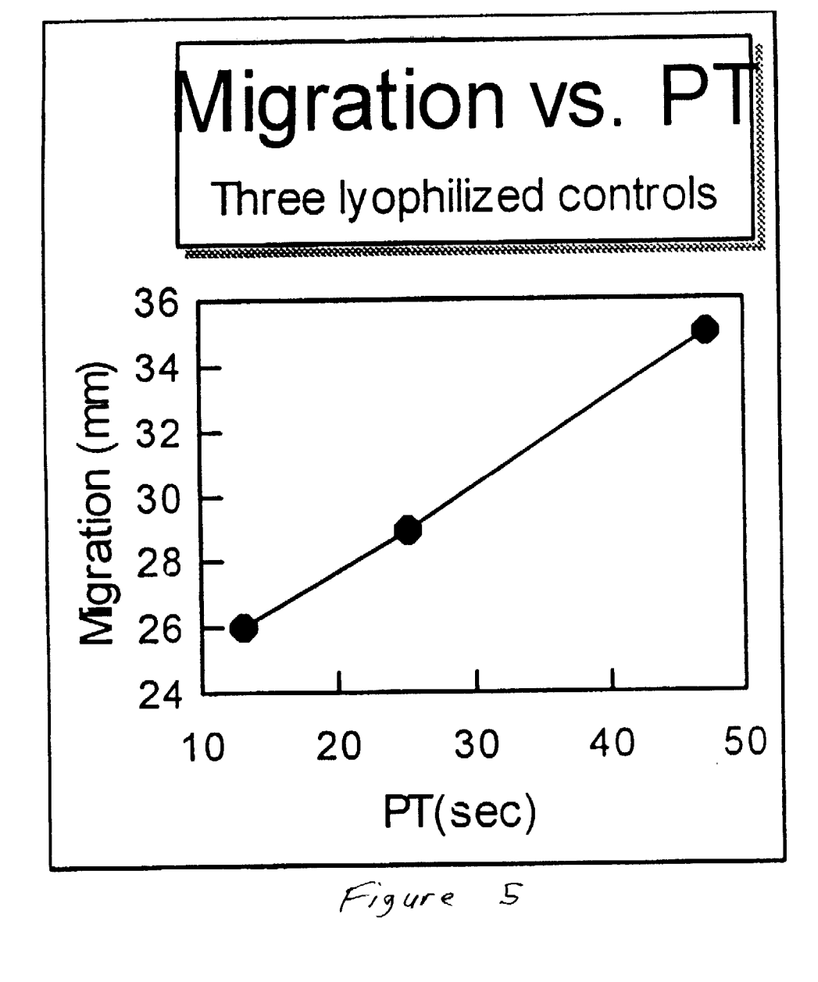
FIGS. 5 and 6 are graphs of migration distance in mm vs. the prothrombin time (PT) in seconds.

Example 3—This experiment, which employs lyophilized controls as in example 1 and 2, a commercial thromboplastin reagent (Instrumentation Labs) and cellulosic paper, also makes use of a timing strip. The thromboplastin and plasma samples were allowed to react for 1.5 minutes prior to contact with the absorbent strips. PT times were determined with a photo-optical instrument (Coag-A-Mate X2, Organon Teknika) instead of a mechanical fibrometer. The results of this test are illustrated in Table 1 and in FIG. 5. Note that a linear correlation is seen between migration in mm and clotting time.

TABLE 1

| Condition | Seconds | Value |
|---|---|---|
| V1 | 13.1 | 26 mm |
| V2 | 25.1 | 29 mm |
| V3 | 47.0 | 35 mm |
| Correlation | | 0.999 |

Figure 6:
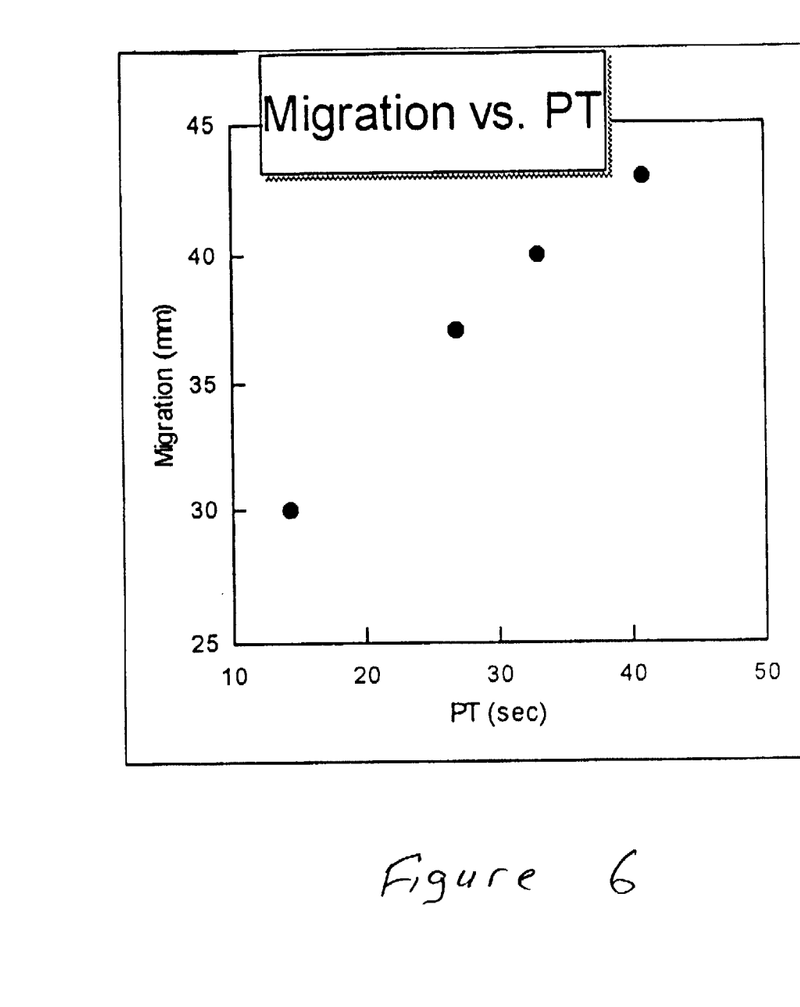

Example 4—In this example, 60 microliters of a thromboplastin reagent prepared from cultured human cells (normal PT=14 seconds) was placed on a square of laboratory film affixed to the surface of the lab bench. Plasma samples (30 microliters) was added to the drop of thromboplastin and allowed to incubate for 60 seconds at room temperature. Samples included three lyophilized control plasmas (Organon Teknika) and one plasma sample taken from a patient on oral anticoagulation (coumadin) therapy. A 5 cm×0.5 cm strip of cotton absorbent paper (Schleicher and Schuell—S/S #903) was then urged into contact with the side of the clotted drop. Serum was observed to move through the paper strip with abnormal plasmas moving further than normal controls. After 3 minutes, the position of the liquid front was marked and measured. Prothrombin times were determined using a fibrometer using standard techniques. The results of this test are illustrated in Table 2 and FIG. 6. This experiment again demonstrates a linear relationship between clotting time and migration for plasmas of diverse coagulation potential.

TABLE 2

Migration in mm vs. PT (fibrometer) in seconds. Absorbent paper is S/S #903. The linear correlation is 0.99, indicating a linear relationship between migration and PT time.

| Sample | mm Migration | PT -fib (Sec) |
|---|---|---|
| V1 | 30 | 14.4 |
| V2 | 37 | 27.0 |
| V3 | 43 | 40.9 |
| coumadin | 40 | 33.0 |
| R^2 | 0.99 | |

Example 5—In another experiment, pooled normal plasma was compared to a single plasma sample from a patient on oral anticoagulant (coumadin) therapy. The experiment used SS #903 paper and a thromboplastin from cultured human cells. A 1 cm difference in migration was observed between the normal and abnormal plasma with the abnormal plasma having the further migration (data not shown). It was found that the measured difference in migration between the normal and abnormal samples increased as strip width decreased.

Figure 7:
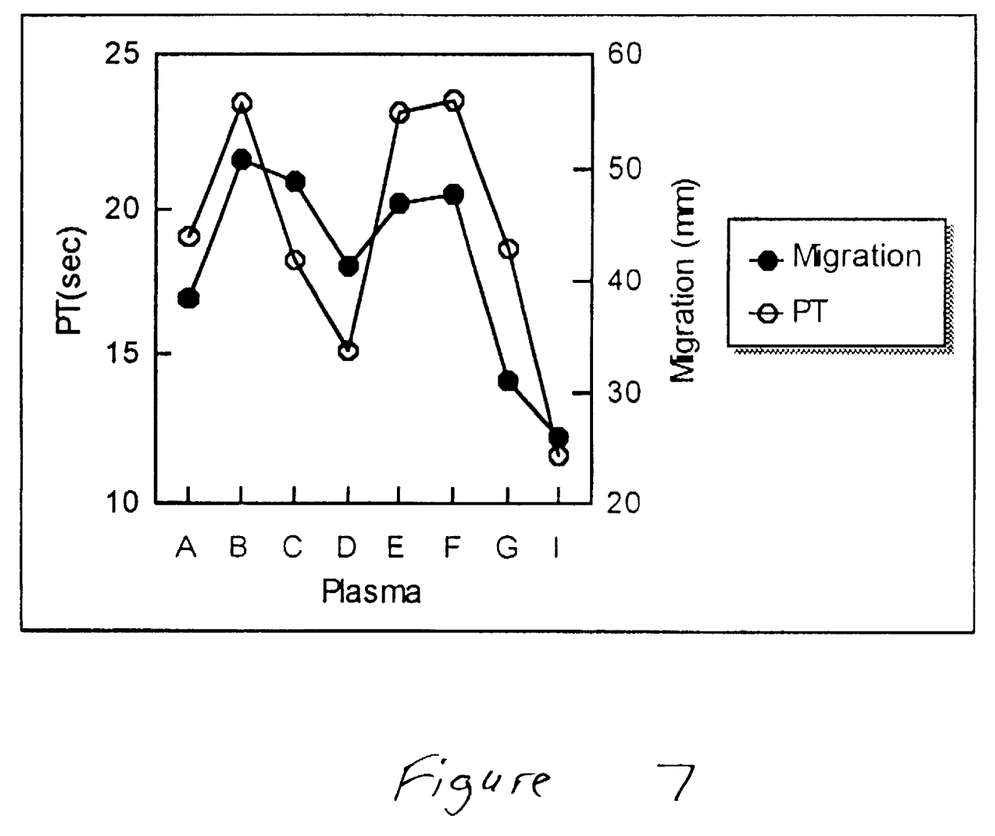
FIG. 7 is a graph showing the relationship between the PT and migration distance for several abnormal plasma samples and one normal plasma sample where the abnormal samples were from patients on oral anticoagulant (coumadin) therapy.

Example 6—In this example, a small panel of plasma samples from patients undergoing oral anticoagulant (coumadin) therapy and a normal plasma sample were examined using the device. Sixty microliters of thromboplastin (Simplastin L, Organon Teknika) was allowed to react with 30 μls of plasma samples for 2.5 minutes before contact with S/S #903 paper, migration and measurement. Prothrombin times were measured using an automated photo-optical device (Coag-A-Mate X2, Organon Teknika). The results of this test are illustrated in FIG. 7, which shows the relation between PT time and distance of migration for the eight plasmas samples. As can be seen in this figure, the general trend in migration follows the PT.

TABLE 3

PT time, INR and migration of several coumadin samples and a normal pool plasma. There is a large separation in migration distance between the normal plasma and the plasma samples that comprise the abnormal panel.

| Plasma | INR | PT | Migration mm |
|---|---|---|---|
| A | 2.5 | 19.1 | 38.5 |
| B | 3.8 | 23.4 | 51.0 |
| C | 2.3 | 18.3 | 49.0 |
| D | 1.6 | 15.1 | 41.5 |
| E | 3.7 | 23.1 | 47.0 |
| F | 3.8 | 23.5 | 48.0 |
| G | 2.4 | 18.7 | 31.0 |
| I (normal) | 0.9 | 11.6 | 26.0 |

Example 8—This example shows the utility of the device with samples exhibiting a blood coagulation factor VII deficiency. Thromboplastin prepared from cultured human cells (normal PT time=25 seconds) was allowed to react for 1.5 minutes with graded mixtures of Factor VII deficient plasma and normal plasma before application of S/S #903 paper. Migration distances were marked at 3,4,5 and 6 minutes. Prothrombin times were determined using standard techniques.

Figure 8:
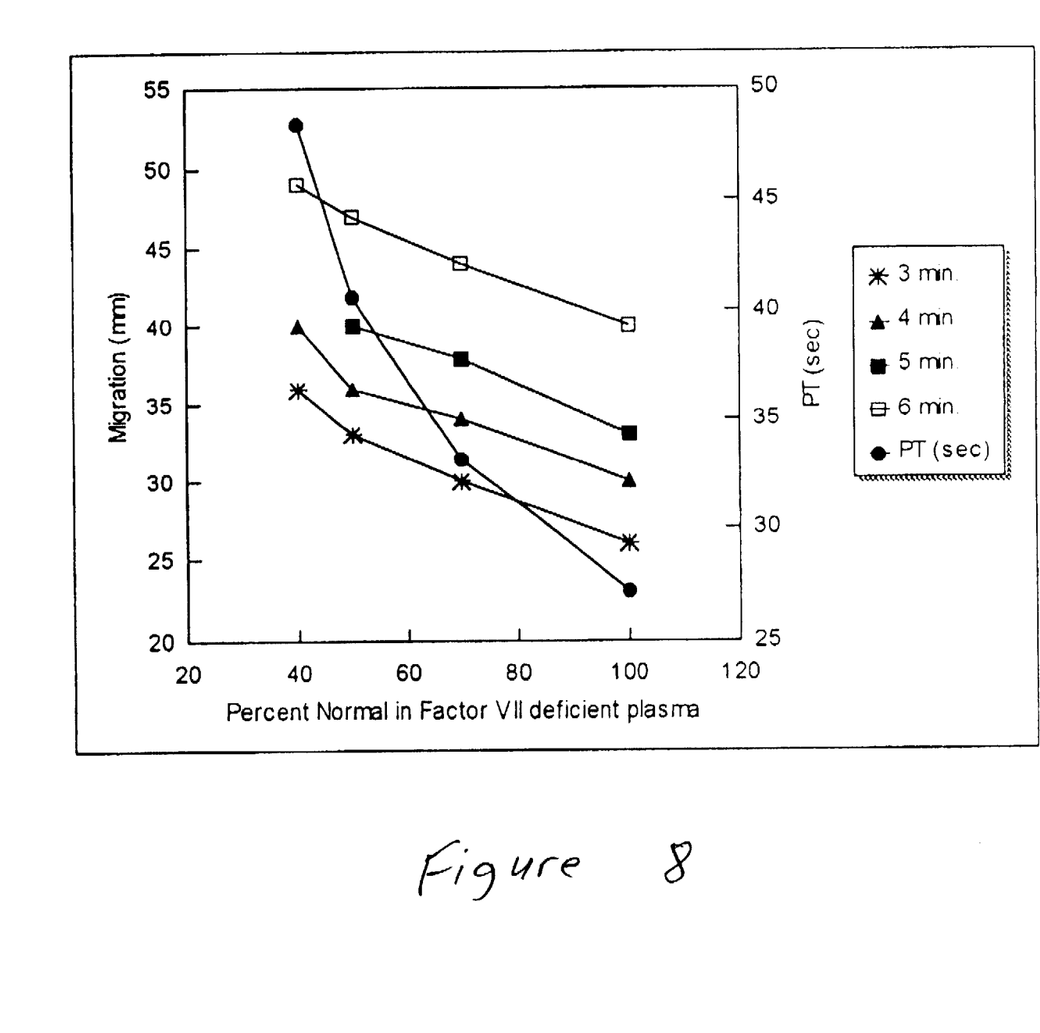
FIG. 8 is a graph showing migration in mm vs. percent normal for a graded mixture of Factor VII deficient plasma in normal plasma as might be done for a factor sensitivity assay.

The results of this test are shown in Table 4 and in FIG. 8. A linear relation between migration distance and PT time was found with all four endpoints. At the final 6 minute endpoint, a linear, four point "factor sensitivity" curve was constructed. Note that a linear relation is found between migration and the percentage of normal plasma without the use of a log transformation. Also note that a log transformation is required to achieve linearity for the prothrombin time vs. percent normal curve.

TABLE 4

Percent normal plasma, PT times, and migration at various endpoint times with S/S #903 paper. After six minutes, no further migration could be detected.

| Percent Normal | PT | 3 min. | 4 min. | 5 min. | 6 min. |
|---|---|---|---|---|---|
| 100 | 27.2 | 26 | 30 | 33 | 40 |
| 70 | 33.1 | 30 | 34 | 38 | 44 |
| 50 | 40.6 | 33 | 36 | 40 | 47 |
| 40 | 48.4 | 36 | 40 | | 49 |

Figure 9:
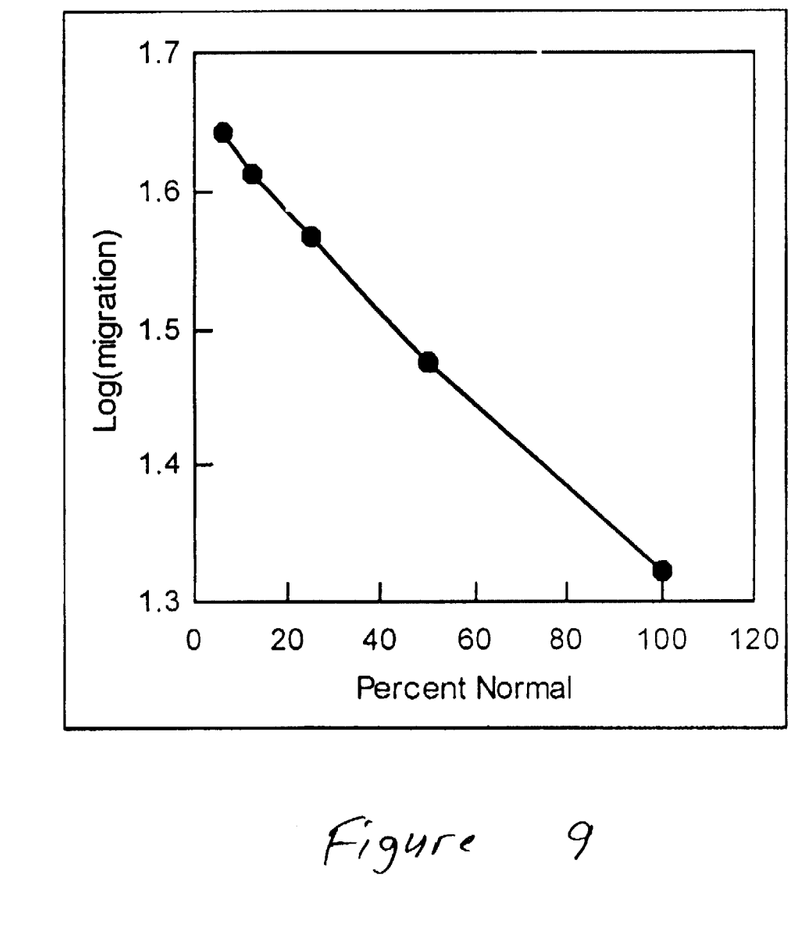
FIG. 9 is a graph showing the log of migration distance vs. percent normal for a graded mixture of normal plasma in saline solution as might be done for a Quick percent assay.

Example 9—Quick percent assays are often used to assess coagulation potential. This example, wherein pooled normal plasma is mixed with buffered saline in various dilutions and tested with the device, shows the utility of the present invention in the Quick percent format. A thromboplastin prepared from cultured human cells (60 microliters) was allowed to react with a plasma sample (30 microliters) for 1 minute and a 50 seconds prior to contact with S/S #903 paper. After 1 minute, migration distance was measured. The results of this test are illustrated in FIG. 9.

Example 10—In order to be used as a generalized coagulation screening device, the present invention must be capable of discriminating (with high sensitivity and specificity) between normal samples and abnormal samples. A particular requirement is utility with abnormal samples from patients stabilized on oral anticoagulant (coumadin) medicines.

In this experiment, 12 coumadin patient plasmas and 6 normal plasmas were analyzed using the present invention.

The thromboplastin (60 microliters) was prepared from cultured human cells (ISI=1.0) and was allowed to react with all samples (30 microliters) for 1 minute and 50 seconds at room temperature prior to contact with 50 mm wide S/S #903 strips. PT times were determined using an automated photo-optical clotting time device (Coag-A-Mate X2, Organon Teknika).

Figure 10:
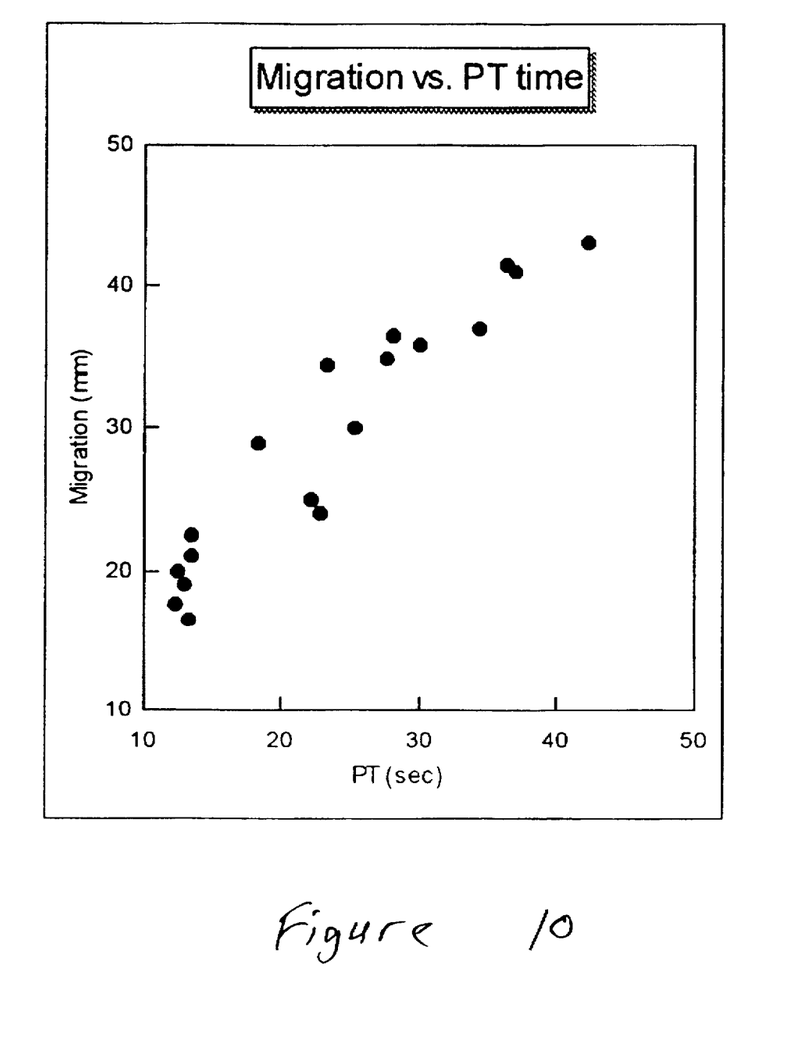
FIG. 10 is a graph showing the correlation between PT time and migration for a panel of normal and abnormal plasmas where the abnormal plasmas are from patients on oral anticoagulant (coumadin) therapy.

The results of this test (Table 5 and FIG. 10) show the good linear correlation between PT time in seconds and migration in millimeters and indicate overall device capability.

TABLE 5

Correspondence between results with a typical photo-optical clotting time device and the present invention.

| Plasma | ID/Lot | X2 PT | Migration |
|---|---|---|---|
| Normal | 2 | 13.3 | 16.5 |
| Normal | 3 | 12.2 | 17.5 |
| Normal | 4 | 13.5 | 22.5 |
| Normal | 5 | 12.5 | 20.0 |
| Normal | 6 | 13.5 | 21.0 |
| Normal | 7 | 12.9 | 19.0 |
| Coumadin | 8 | 36.5 | 41.5 |
| Coumadin | 9 | 25.2 | 30.0 |
| Coumadin | 10 | 28.1 | 36.5 |
| Coumadin | 11 | 37.0 | 41.0 |
| Coumadin | 12 | 23.2 | 34.5 |
| Coumadin | 13 | 42.4 | 43.0 |
| Coumadin | 14 | 18.4 | 29.0 |
| Coumadin | 15 | 22.2 | 25.0 |
| Coumadin | 16 | 30.0 | 36.0 |
| Coumadin | 17 | 22.8 | 24.0 |
| Coumadin | 18 | 34.5 | 37.0 |
| Coumadin | 19 | 27.6 | 35.0 |

Figure 11:
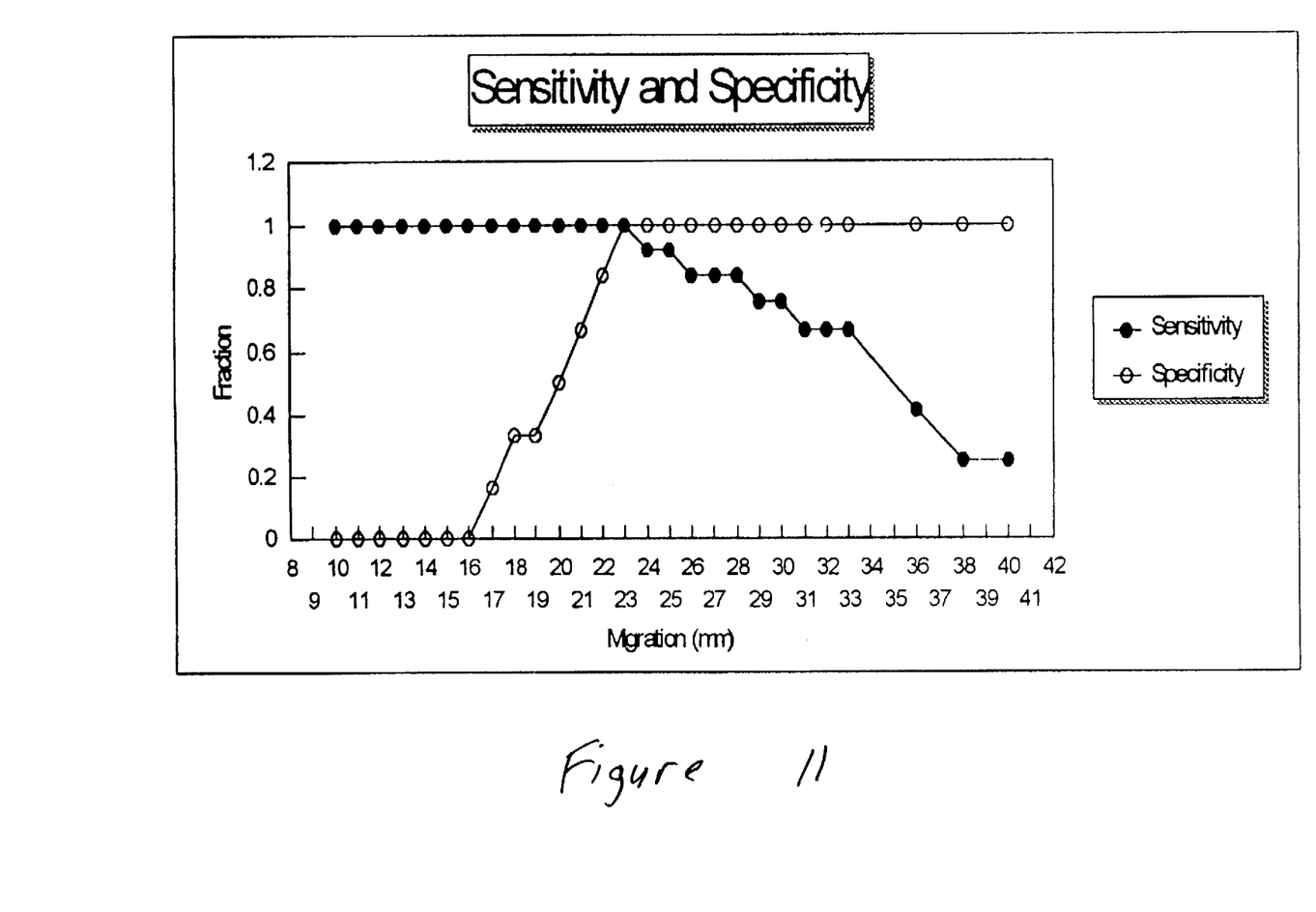
FIG. 11 is a graph of the calculated sensitivity and specificity from FIG. 10.

FIG. 11 depicts sensitivity and specificity for each sample pair plotted on the same graph. At a migration distance of 23 mm, the device shows perfect sensitivity and specificity towards normals and abnormal samples. The invention was able to clearly distinguish normals from abnormals with high sensitivity and specificity. Conversion of the data to INR units indicates that the present invention works in an INR range of from 1 to 4 (a clinically useful operable range).

Figure 12:
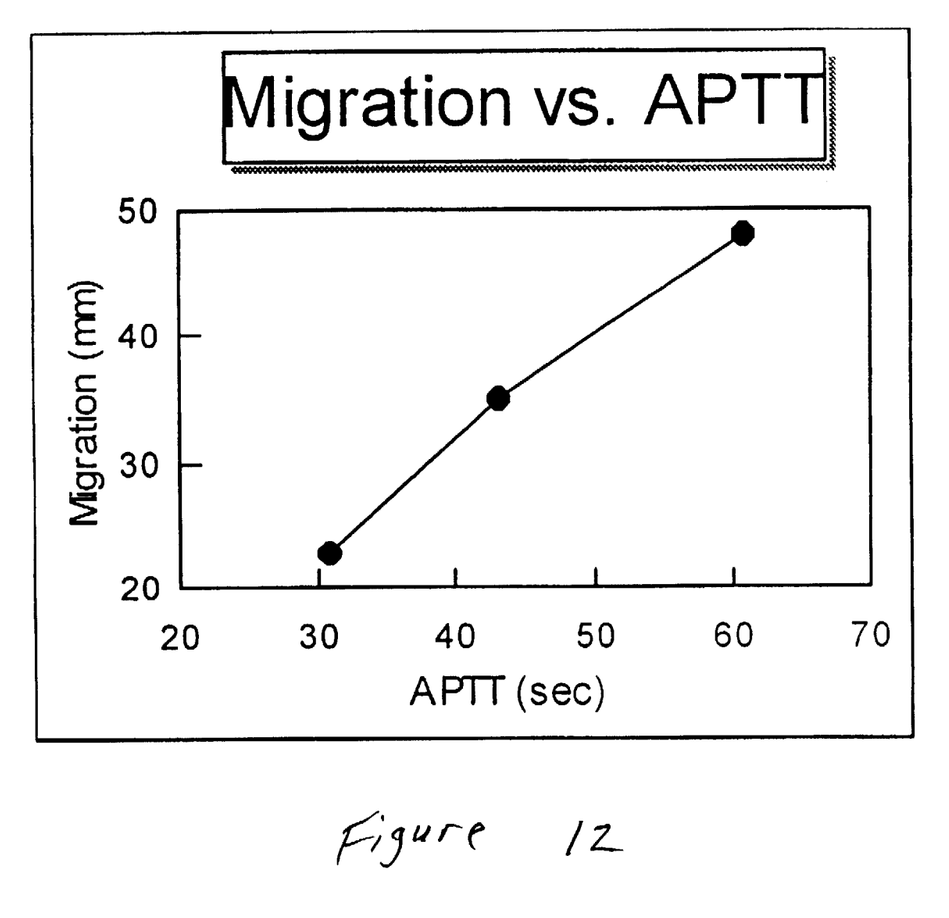
FIG. 12 is a graph of migration distance vs. the activated partial thromboplastin time (APTT) where three lyophilized controls are caused to clot using APTT reagents and allowed to migrate through the absorbent strip.

Example 11—In the prior examples, thromboplastin reagents are used to effect clotting of the plasma samples prior to application of the absorbent membrane. In this example, silica, phospholipids and calcium are used to effect clotting as for a routine APTT test. Thirty microliters of APTT activator (Organon Teknika) is added to 50 microliters each of lyophilized control plasma samples and allowed to react for 5 minutes. After the activation period, 30 microliters of calcium chloride solution (Organon Teknika) is applied to the mixture and allowed to react for 2.5 minutes prior to application of a 0.5 cm wide strip of S/S #903 absorbent paper. After 2 minutes, migration distances are measured and correlated to the APTT as determined on a fibrometer for the same reagents and plasma samples. Results of this test are included as FIG. 12 where it is seen that a good linear correlation exists between migration distance and the APTT time using the present invention.

Other features of benefit that can be applied to the embodiments shown in FIG. 1 or FIG. 2 are as follows. A non-retained dye can be used to clearly delineate the front, making the device easy to read. The absorbent material can be impregnated with a virucidal agent to inactivate infectious agents (e.g. hepatitis or HIV). An electronic platform with heater and timer can be included within the present invention. The invention can include an area for placement of a bar code and/or a surface for marking. The invention can be used in many different orientations and does not have to be used on a flat surface. The device can be made the size of a credit card.

It is to be understood that the invention described and illustrated herein is to be taken as a preferred example of the same, and that various changes in the method and apparatus of the invention may be resorted to, without departing from the spirit of the invention or scope of the claims.

I claim:

1. A method for determining whether a patient has a normal or abnormal blood coagulation potential, comprising:

obtaining a blood sample from a patient;

combining said blood sample with a clotting agent to initiate clotting;

waiting for a period of time to allow clotting to take place such that said blood sample turns into a blood clot and liquid serum;

bringing said liquid serum into contact with an absorbent material so that said serum migrates through said absorbent material a particular distance;

determining the distance of migration of the serum, said distance being proportional to a blood clot time of the patient; and determining, based on said determined distance of migration, whether said patient has a normal or abnormal blood coagulation potential.

2. The method according to claim 1, wherein said clotting agent comprises an APPT reagent or a thromboplastin reagent.

3. The method according to claim 2, wherein said clotting agent comprises a thromboplastin reagent containing the enzyme tissue factor and calcium ions.

4. The method according to claim 2, wherein said clotting agent comprises an APPT reagent containing silica, phospholipids and calcium ions.

5. The method according to claim 1, wherein said absorbent material comprises at least one of cotton fibers and cellulose fibers.

6. The method according to claim 5, wherein said absorbent material comprises cotton fibers with predetermined serum uptake properties.

* * * * *